United States Patent
Zimmermann

(10) Patent No.: US 6,793,391 B2
(45) Date of Patent: Sep. 21, 2004

(54) SYSTEM AND METHOD FOR SENSOR POSITIONING

(75) Inventor: Jurgen Zimmermann, Biebesheim (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 10/644,982

(22) Filed: Aug. 21, 2003

(65) Prior Publication Data

US 2004/0091083 A1 May 13, 2004

Related U.S. Application Data

(63) Continuation of application No. PCT/DE02/00635, filed on Feb. 21, 2002.

(51) Int. Cl.$^7$ .................................................. A61B 6/14
(52) U.S. Cl. ......................................... 378/205; 378/38
(58) Field of Search ............................ 378/205, 38, 39, 378/98.5, 168, 170

(56) References Cited

U.S. PATENT DOCUMENTS

| | | | |
|---|---|---|---|
| 2,557,428 A | * 3/1951 | Grostic | 33/1 |
| 4,131,998 A | 1/1979 | Spears | 33/1 |
| 4,475,224 A | 10/1984 | Grassme | 378/38 |
| 4,630,375 A | 12/1986 | Spolyar | 33/1 B |
| 4,907,251 A | 3/1990 | Mork et al. | 378/39 |
| 5,049,748 A | 9/1991 | Ito et al. | 250/327.2 |
| 5,195,114 A | 3/1993 | Sairenji et al. | 378/40 |
| 5,267,296 A | 11/1993 | Albert | 378/113 |
| 5,444,754 A | 8/1995 | Wederhorn et al. | 378/38 |
| 5,490,197 A | 2/1996 | Albert et al. | 378/133 |
| 5,513,252 A | 4/1996 | Blaschka et al. | 378/98.8 |
| 6,188,744 B1 | 2/2001 | Shinohara et al. | 378/8 |
| 6,477,223 B1 * | 11/2002 | Francke | 378/19 |

FOREIGN PATENT DOCUMENTS

DE            33 30 116         5/1984

* cited by examiner

Primary Examiner—David V. Bruce
Assistant Examiner—Chih-Cheng Glen Kao
(74) Attorney, Agent, or Firm—Dykema Gossett PLLC

(57) ABSTRACT

The invention relates to a device for determining and/or positioning a sensor of a digital X-ray unit. The device includes an input and output unit, which serve to interactively control the device, and further includes a first storage location in which a digital picture of an area to be examined is stored. The device also includes a second storage location, in which at least one template-shaped image of the sensor is stored, and further includes a processing unit that simulatively places the template-shaped image of at least one sensor onto an area of the digital picture to be examined whereby completely displaying the area to be examined in the event of an actual X-ray picture.

22 Claims, 2 Drawing Sheets

SYSTEM AND METHOD FOR SENSOR POSITIONING

CROSS REFERENCE TO RELATED APPLICATION

This s a continuation of International Application PCT/DE02/00635 filed Feb. 21, 2002, which designated the U.S. All priorities are claimed.

BACKGROUND OF INVENTION a. Field of Invention

The invention relates to a system and method for specifying and positioning a sensor of digital X-ray apparatus.

b. Description of Related Art

The production of digital intraoral images using an intraoral sensor is disclosed in EP 0 643 901 (U.S. Pat. No. 5,513,252). The features disclosed in said document are incorporated in this application by reference.

In the field of dental digital X-ray examination there is a large number of various sensor sizes and shapes for producing intraoral images. The selection of these sensors is usually guided by experience. Experience, however, is frequently based on invalid tests.

Thus a larger sensor might be more suitable than a smaller one in certain X-raying situations. In other cases the point to be examined would be easier to reach, from an anatomical point of view, by using a smaller sensor. Furthermore, the decision must be made as to how the desired objects can be X-rayed using a smaller sensor.

Particularly in the case of individual series of radiograms of one patient, it has previously been difficult to judge how many images should be produced and what teeth should, if possible, be X-rayed together in order to minimize the radiation impact by lowering the number of X-ray images.

It is an object of the invention to provide a system and method for simplifying the selection of sensors from the outset.

SUMMARY OF INVENTION

This object is achieved by a system and method having the features of the independent claims. Specifically, as shown in FIG. 2, the aforementioned objects are achieved by a system for specifying the position of a sensor 14 of a digital X-ray apparatus, which system exhibits input and output devices 8 for interactive control of the system. These devices preferably comprise a graphics system on which digitized X-ray photographs and X-ray images can be shown and keyboards and pointing devices. The system has a first storage area 9, in which a digital image of an area to be examined is stored. In this case the image is ideally an individual general image in the form of a panoramic radiogram of the patient to be examined. If no such image should be present, the system offers a selection of patterns, from which that can be selected which matches the patient best.

In a second storage area 10, which may physically coincide with the first storage area, there are stored as many template images of the sensors as there are sensors or possible arrangements of sensors. The templates are displayed such that they comply with the shape and size of the image of the relevant sensor.

Another component of the system is a processing unit 11 which places the template image of at least one sensor simulatively on the area of the digital image which is to be examined such that in the case of a real X-ray image the region to be examined is imaged completely. Said processing unit is preferably a known processor. The processor can either carry out fully automatic determination, in which case a previously specified area is covered, as a result of matching computation based on the shape and coordinates of the templates, so well that a minimum amount of radiation is necessary. Optimization is effected in observance of the criterion that the overlap should be as small as possible, for by this means the patient is exposed only to that radiation dosage which is just necessary.

The processing unit furthermore has means for displaying the sensor and the position of the sensor in the digital image, for which purpose the output device, in particular, is provided. This makes it possible for the user to ascertain the sensor specified by the processing unit, and the position of the sensor.

The system has in its preferred form a user interface 16 enabling interactive selection of the template image and/or the area to be examined. This makes it possible for the user to be interactively engaged in the specifying procedure. One possible user interface is a graphical interface of a computer on which the image is displayed. Selection boxes make it possible to select different templates, which can then be moved to the area to be examined by means of a pointing device, such as a mouse. The area to be examined must be specified for filly automatic determination. This can likewise take place by specifying points with the aid of a pointing device. In the case of completely manual selection, the digital template is passed over the area, which is then preferably displayed in a different color. It is particularly advantageous when only those objects forming part of the image which are to be examined are made particularly distinguishable, ie, for example, when only the teeth are high-lighted.

If the image should contain information concerning several dimensions, the position of the template image relative to the X-ray image can possibly be specified in one or more dimensions. To this end the image is in the form of a multidimensional object, in particular a two-dimensional area having an additional dimension determining down/up, right/left, or rotated alignment.

By way of a computer interface 12 to the X-ray apparatus the thus determined presettings are transferred to the X-ray apparatus, which permits the production of a digital image only when these presettings prevail. Thus the X-ray apparatus can block X-raying until the correct sensor has been selected. This information can be provided by coding the sensors and using corresponding contacts in the sensor mount.

To remove the necessity of having to work with templates only, the system has a computer interface 13 via which digital images of the patient to be X-rayed are transferred to the first storage area. This ensures that very precise presettings will be used and the selection will be matched to anatomic peculiarities.

The X-ray apparatus used is preferably a dental X-ray unit. The system is preferably in the form of a PC controlled by software, which carries the method defined in the claims stated below into effect.

Another component of the present invention comprises digital or mechanical templates for specifying a digital X-ray sensor complying in shape and size to an X-ray image made with the assigned digital X-ray sensor. This makes it possible, by mechanically shifting the template over an existing image, to ascertain what sensor will be most suitable for a future image.

The template is preferably designed such that it can be moved across an X-ray image without restricting the visible area of the image. This may be effected, for example, by the use of a frame and/or transparent material 15.

The invention also relates to a method of specifying and/or positioning a sensor of digital X-ray apparatus by means of templates complying in size and shape to the sensor image. The method has a first step in which an X-ray image is selected, this being preferably an X-ray image of the patient to be examined. In the second step, the area to be depicted is determined. This area can either be one digitally predetermined or one specified by the user by image a frame around the object to be X-rayed. In a third step, there is selected, from a plurality of templates of which each is assigned to a sensor of the digital X-ray apparatus, that template which covers the area specified in the second step most precisely. For subsequently creating the image, that sensor is selected to which the template determined in the third step is assigned.

Selection of the template may be carried out either automatically or interactively.

In a preferred embodiment, the X-ray images and the templates are managed in digital form.

The invention also relates to software for effecting the said method.

Yet another component of the invention is a data medium having a data structure that is capable of running on a computer to effect the method described above.

BRIEF DESCRIPTION OF THE DRAWINGS

The accompanying drawings, which are included to provide a further understanding of the invention and are incorporated in and constitute a part of this specification, illustrate preferred embodiments of the invention and together with the detail description serve to explain the principles of the invention. In the drawings.

DETAILED DESCRIPTION OF THE PREFERRED EMBODIMENTS

Other advantageous embodiments are defined in the subclaims. A detailed description is given below with reference to the image. The only FIGURE shows the method steps involved in the selection and arrangement of templates.

WORKING EXAMPLE

Figure 1:
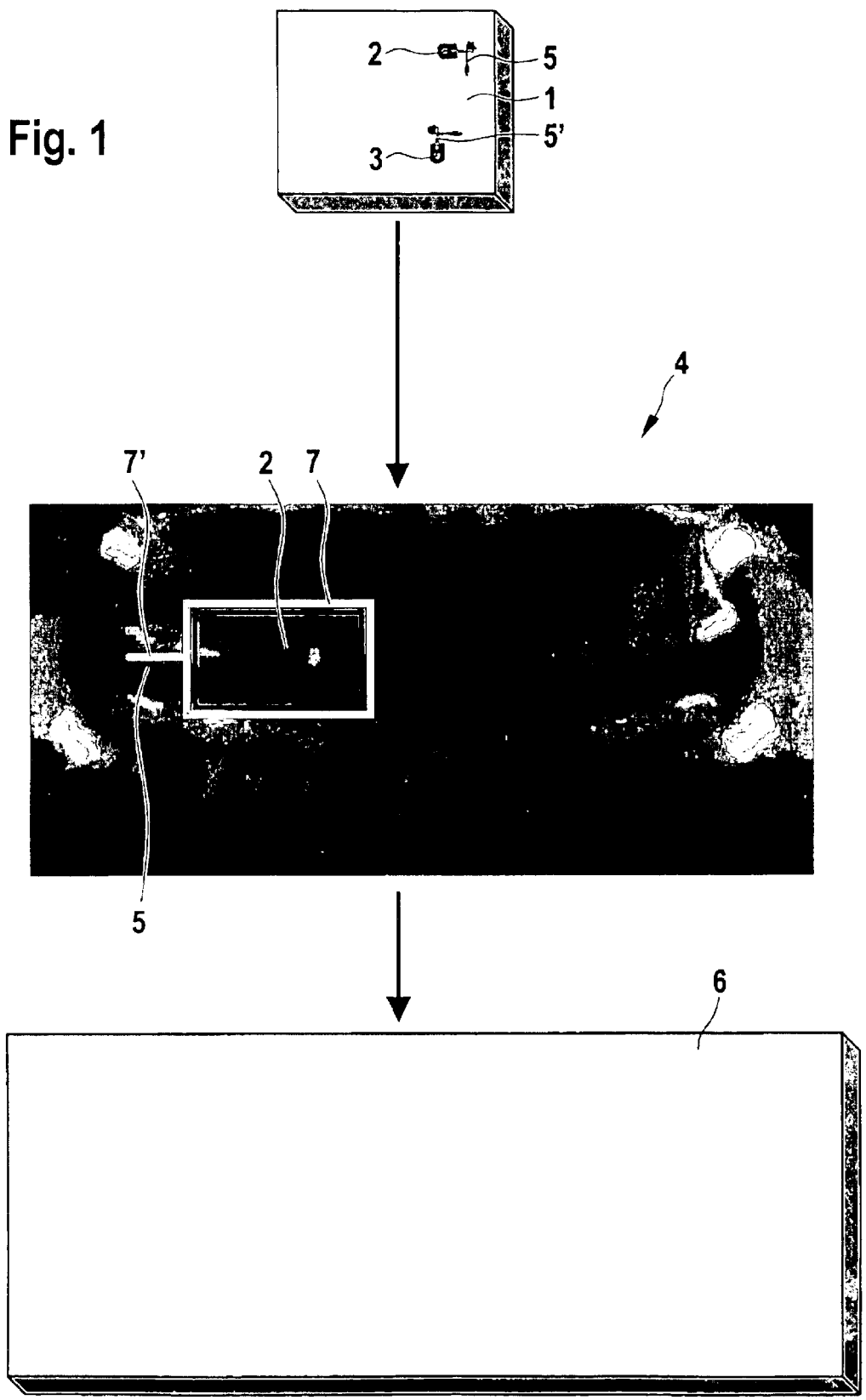
FIG. 1 illustrates a selection area in which a number of sensor templates are ready for selection.
Figure 2:
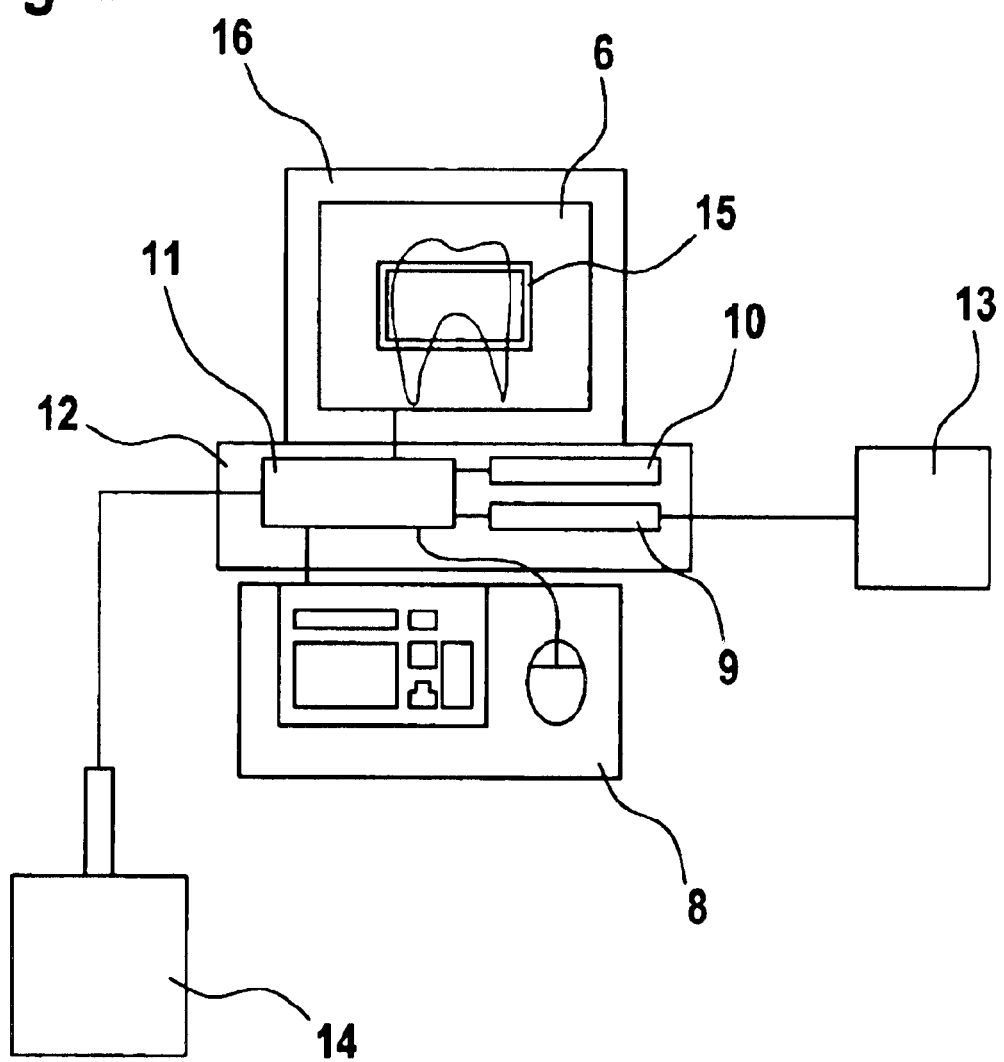
FIG. 2 illustrates the various components for a system according to the present invention for determining and/or positioning a digital sensor of a dental X-ray apparatus.

FIG. 1 shows a selection area 1, in which a number of sensor templates 2, 3 is ready for selection, said templates being in the form of images of a digital intraoral sensor showing different alignments, ie template 2 is horizontally aligned and template 3 is vertically aligned. Furthermore, the templates can represent sensors of different sizes. In addition to the sensors, the position of the cable 5,5' is also given.

A template can be selected from this selection area 1 by, for example, dragging it onto a digitized X-ray image 4 (drag & drop). Here the template is displayed in its actual size or scaled up by a factor corresponding to the X-ray image and can be positioned by input means until the desired area of the patient to be X-rayed lies sufficiently within the template 2. It can be ascertained whether the selected template is unsuitable for making the desired image, whereupon another template, and thus another sensor or a different spatial alignment of the sensor, is selected and superimposed on the X-ray image 4. The representation of the sensor in the X-ray image is effected such that the cable duct 5 of the sensor is taken into account and is automatically oriented when the sensor is positioned such that the cable forms no hindrance. This is effected by turning the sensor through 180° when certain ranges are exceeded. This alignment of the template 2 also makes it possible to achieve correct positional alignment of the X-ray image produced in that the X-ray image coming from sensor 2 is rotated and/or tilted in accordance with the planned imaging position.

A display area 6 then imparts a rough idea of the X-ray image to be expected. When the image has been produced, the display area 6 displays the X-ray image obtained, for purposes of control with reference to the result of the action, and particularly to ascertain whether the areas of interest have in fact been imaged.

The X-ray image 4 can be a standardized X-ray photograph which may or may not have been selected to take into consideration the age, size, sex, and race of the patient. However, the image is ideally a stored panoramic image of the patient, of which a new partial image of an area of special interest is to be made.

As described above, the method can alternatively proceed such that first of all the area of interest is selected and then a proposal as to which of the sensors is suitable for imaging the selected area appears automatically. Account is taken of the fact that the selected regions must all be discernible in the image, overlapping images being proposed for larger areas.

In addition to making individual images, it is a simple matter to make a series of radiograms by supporting simultaneous preselection of several areas to be X-rayed. It is possible to select several areas in the X-ray image 4 which are not connected, whereupon a proposal for the use of the respective sensors assigned to the areas in respective spatial alignment appears and an imaging procedure is proposed. It is always possibly to carry out subsequent manual correction of the proposals to take into consideration anatomic peculiarities, such as a flat palate.

If it should be necessary to introduce a holder for the sensor into the oral cavity, a suitable selection can be indicated by an appropriate color of a frame 7, having cable routing 7', surrounding a sensor 2. Other indicating means can be used for this purpose, if desired.

What is claimed is:

1. A system for determining and/or positioning a digital sensor of a dental X-ray apparatus, comprising:

an input and output device for interactive control of the system, a first storage area, in which a digital image of an area to be examined, is saved, a second storage area, in which a plurality of template images corresponding to different sensors of the dental X-ray apparatus are stored, and a processing unit, which places a selected template image of a sensor simulatively on the area to be examined of the digital image such that when a real X-ray image is created, the area to be examined is depicted completely and precisely, wherein the processing unit has means for indicating the sensor and the position of the sensor in the digital image.

2. A system as defined in claim 1, further comprising a user interface enabling interactive selection of the template images and/or the area to be examined.

3. A system as defined in claim 1, wherein a user interactively specifies the area to be examined in the digital image, and the processing unit specifies that template image which covers the area to be examined as completely as possible.

4. A system as defined in claim 1, wherein the processing unit determines the position of the template images in one or more dimensions.

5. A system as defined in claim 1, further comprising a computer interface to the X-ray apparatus, via which presettings determined by simulation are transferred, while the X-ray apparatus permits the creation of a digital image only when said presettings apply.

6. A system as defined in claim 1, further comprising a computer interface, via which an existing digital image of a patient to be X-rayed is transferred to the first storage area.

7. A system as defined in claim 1, wherein the apparatus comprises a dental X-ray-unit.

8. A system as defined in claim 1, wherein the system comprises a PC controlled by software.

9. A data medium containing a data structure including a template for specifying a digital X-ray sensor, said template comprising a shape and size of an X-ray image in the form of a digital X-ray sensor, said size and shape of said template being scaled up by a factor corresponding to the X-ray image for displaying said X-ray image.

10. A data medium as defined in claim 9, further comprising a property making it possible top pass the template over an X-ray image.

11. A data medium as defined in claim 10, further comprising a digitally stored size and orientation which is adapted, when called on, in accordance with actual dimensions of a digital X-ray image.

12. A method of specifying and/or positioning a digital sensor of a dental X-ray apparatus using templates corresponding in size and shape to a sensor image, comprising:

a first stop, in which an X-ray image is selected, this being an X-ray image of a patient to be examined, a second step, during which an area to be imaged is specified, and a third step, during which there is selected, from a plurality of templates each of which is assigned to sensors of the dental X-ray apparatus, that template which covers the area specified in the second step most precisely.

13. A method as defined in claim 12, wherein the third step is carried out automatically or interactively.

14. A method as defined in claim 12, wherein the X-ray image and the templates are managed in digital form.

15. A data medium, containing a data structure that is capable of running on a computer to carry a method as defined in claim 12.

16. A method for specifying and/or positioning a digital sensor of a dental X-ray apparatus, using templates corresponding in size and shape to an image of the sensor, comprising:

a first step, in which an X-ray image is selected, this being an X-ray image of a patient to be examined, a second step, during which there is selected, from a plurality of templates each assigned to a sensor of the dental X-ray apparatus, that template which should be used to cover an area to be X-rayed, and a third step, during which the selected template is moved across the X-ray image for purposes of control and an imaging urea appertaining to the selected template is thus revealed, the second and third steps being iteratively continued until a suitable combination of sensor and imaging area is displayed.

17. A method as defined in claim 16, wherein the X-ray image and the templates are managed in digital form.

18. A data medium, containing a data structure that is capable of running on a computer to carry a method as defined in claim 16.

19. A method for creating a number of partial images using a plurality of sensors, comprising a first step in which several areas to be X-rayed are selected from an image, and a second step in which there is effected automatic selection and display of at least one sensor suitable for creating a respective image.

20. A method as defined in claim 19, wherein the image is a digital panoramic radiogram, which is displayed on a digital display unit and refers individually to a patient.

21. A method as defined in claim 19, wherein a suitable sequence for making images is automatically proposed, account being taken of particular conditions of a respective X-raying situation, said account being at least one of the order of images to be created, operation of positioning an X-ray unit, and selection of a sensor type.

22. A data medium, containing a data structure that is capable of running on a computer to carry a method as defined in claim 19.

* * * * *